(12) United States Patent
Rodriguez et al.

(10) Patent No.: US 11,690,573 B2
(45) Date of Patent: Jul. 4, 2023

(54) SYSTEMS FOR SKIN PATCH GRAVITY RESISTANCE

(71) Applicant: MEDTRONIC MINIMED, INC., Northridge, CA (US)

(72) Inventors: Jasson Rodriguez, Rosemead, CA (US); Ellis Garai, Studio City, CA (US); Ravi R. Deverkadra, Simi Valley, CA (US); Sara M. Voisin, Chatsworth, CA (US); Jacob E. Pananen, Santa Monica, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 758 days.

(21) Appl. No.: 16/719,892

(22) Filed: Dec. 18, 2019

(65) Prior Publication Data
US 2021/0186424 A1 Jun. 24, 2021

(51) Int. Cl.
*A61B 5/1455* (2006.01)
*A61B 5/00* (2006.01)
*A61B 5/145* (2006.01)

(52) U.S. Cl.
CPC .......... *A61B 5/688* (2013.01); *A61B 5/14532* (2013.01); *A61B 5/6848* (2013.01)

(58) Field of Classification Search
CPC .......................... A61B 5/1455; A61B 5/14532
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |

(Continued)

FOREIGN PATENT DOCUMENTS

| | | |
|---|---|---|
| CN | 208582728 U | 3/2019 |
| EP | 3396356 A1 | 10/2018 |
| WO | 2019020441 A1 | 1/2019 |

*Primary Examiner* — Marjan Fardanesh
(74) *Attorney, Agent, or Firm* — Foley & Lardner LLP

(57) ABSTRACT

A system for a physiological characteristic sensor deployed with a sensor inserter includes an adhesive skin patch coupled to the physiological characteristic sensor. The adhesive patch is to couple the physiological characteristic sensor to an anatomy. The system also includes a gravity resistance system coupled to the adhesive patch and to be coupled to the sensor inserter. The gravity resistance system maintains the adhesive patch substantially perpendicular to a longitudinal axis of the sensor inserter prior to deployment of the physiological characteristic sensor and is removable from the adhesive patch by the sensor inserter upon deployment of the physiological characteristic sensor.

10 Claims, 9 Drawing Sheets

(56) References Cited

U.S. PATENT DOCUMENTS

| | | |
|---|---|---|
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,892,085 B2 | 5/2005 | McIvor et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,468,033 B2 | 12/2008 | Van Antwerp et al. |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,295,786 B2 | 3/2016 | Gottlieb et al. |
| 2007/0123819 A1 | 5/2007 | Mernoe et al. |
| 2009/0299301 A1 | 12/2009 | Gottlieb et al. |
| 2010/0160861 A1 | 6/2010 | Causey, III et al. |
| 2013/0131468 A1 | 5/2013 | Deck |
| 2013/0267811 A1 | 10/2013 | Pryor et al. |
| 2015/0245799 A1 | 9/2015 | Gretz et al. |
| 2016/0058380 A1 | 3/2016 | Lee et al. |
| 2017/0112534 A1 | 4/2017 | Schoonmaker et al. |
| 2017/0188912 A1 | 7/2017 | Halac et al. |
| 2017/0290533 A1 | 10/2017 | Antonio et al. |
| 2019/0060511 A1 | 2/2019 | Larson |

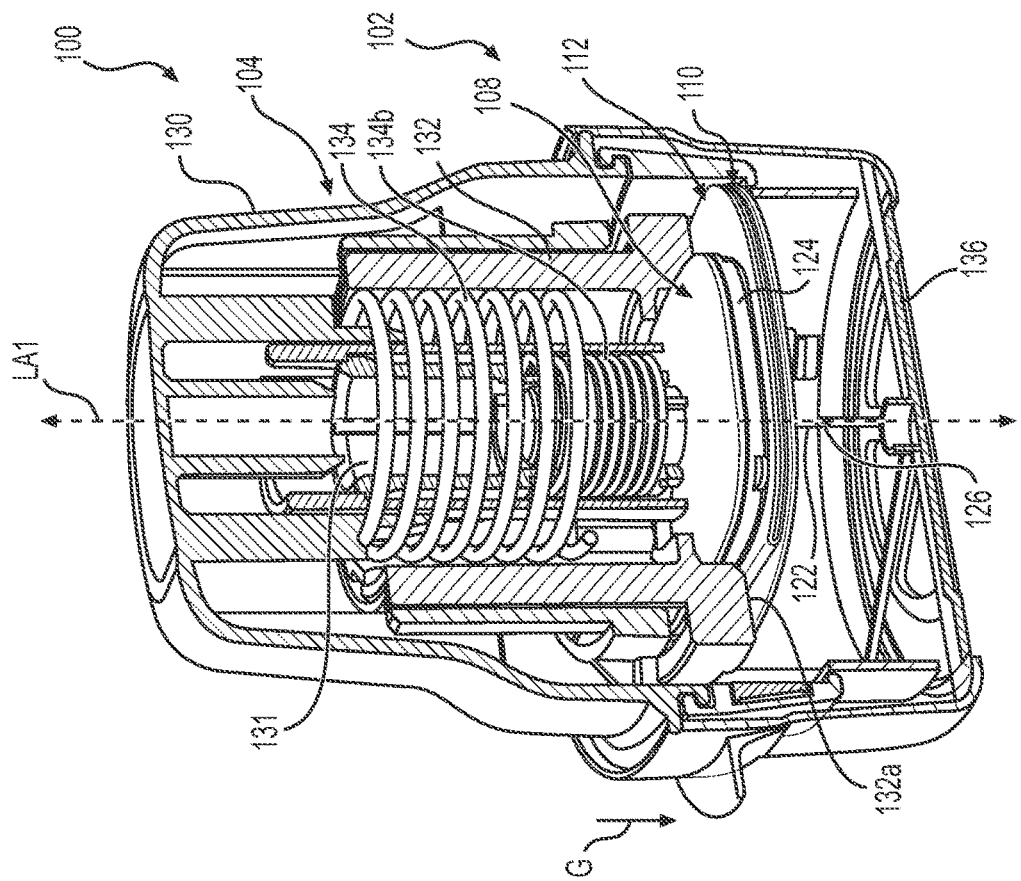
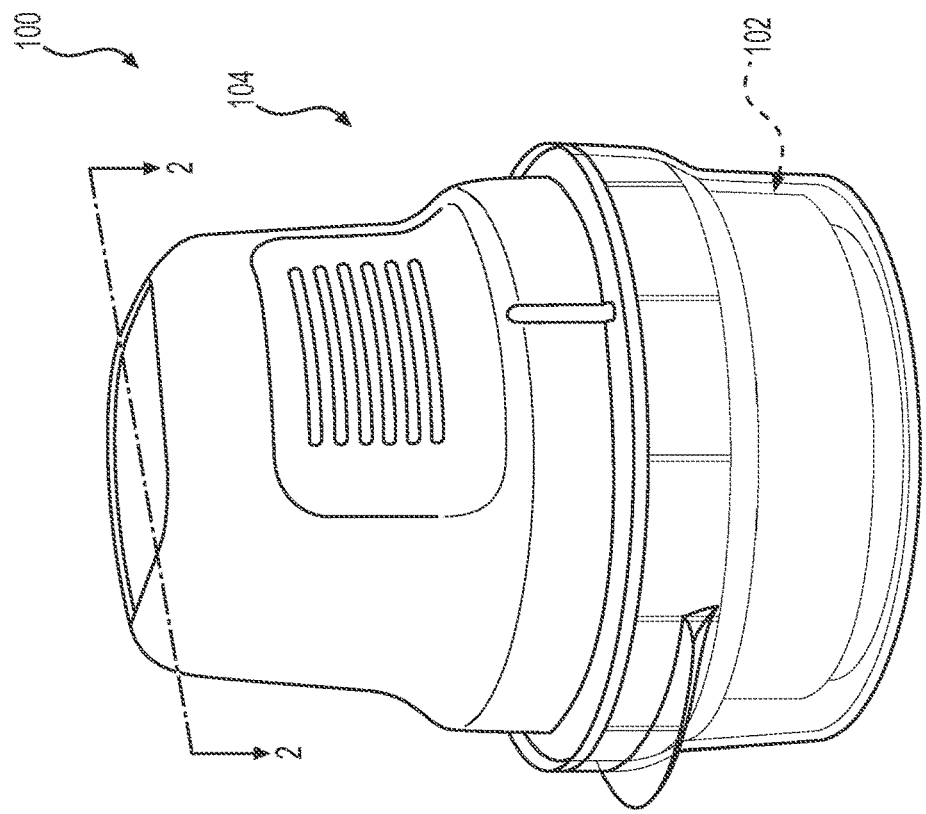

SYSTEMS FOR SKIN PATCH GRAVITY RESISTANCE

FIELD

Embodiments of the subject matter described herein relate generally to medical devices, such as a skin patch for a physiological characteristic sensor assembly. More particularly, embodiments of the subject matter relate to systems that improve gravity resistance of a skin patch during storage to ensure that the skin patch remains ready for coupling to a user after a period of time.

BACKGROUND

Sensors may be employed in the treatment of or monitoring of various medical conditions. In one example, thin film electrochemical sensors are used to test analyte levels in patients or users. More specifically, thin film sensors have been designed for use in obtaining an indication of blood glucose (BG) levels and monitoring BG levels in a diabetic user, with the distal segment portion of the sensor positioned subcutaneously in direct contact with extracellular fluid. Such readings can be especially useful in adjusting a treatment regimen which typically includes regular administration of insulin to the user.

A glucose sensor of the type described above may be packaged and sold as a product, such as a continuous glucose monitor, which is adhered to the patient during use via an adhesive skin patch. In certain instances, the continuous glucose monitor may be packaged with a sensor introducer tool, which enables the implantation of the glucose sensor subcutaneously/transcutaneously. The sensor introducer tool contains a needle that is used to puncture the skin of a user at the same time as the sensor is introduced. The needle is then withdrawn, leaving the sensor in the skin of the user.

In instances where the continuous glucose sensor is packaged with the sensor introducer tool, the continuous glucose sensor may be positioned within the sensor introducer tool such that the skin patch is subjected to the effects of gravity. Gravity, when acting on the skin patch, may cause the skin patch to droop or sag within the sensor introducer tool. When the skin patch droops or sags within the sensor introducer tool, the skin patch may fold upon itself, and thus, may not adhere well to the user.

Accordingly, it is desirable to provide systems for improving gravity resistance of a skin patch, such as a skin patch coupled to a physiological characteristic sensor, for example, a glucose sensor or continuous glucose monitor, which inhibits the skin patch from drooping or sagging to ensure that the skin patch remains ready for coupling to a user after a period of time. Furthermore, other desirable features and characteristics will become apparent from the subsequent detailed description and the appended claims, taken in conjunction with the accompanying drawings and the foregoing technical field and background.

BRIEF SUMMARY

The techniques of this disclosure generally relate to systems that improve gravity resistance of an adhesive skin patch, such as an adhesive skin patch coupled to a medical device, such as a glucose sensor or continuous glucose monitor.

Provided according to various embodiments is a system for a physiological characteristic sensor deployed with a sensor inserter. The system includes an adhesive patch coupled to the physiological characteristic sensor. The adhesive patch is to couple the physiological characteristic sensor to an anatomy. The system also includes a gravity resistance system coupled to the adhesive patch and to be coupled to the sensor inserter. The gravity resistance system maintains the adhesive patch substantially perpendicular to a longitudinal axis of the sensor inserter prior to deployment of the physiological characteristic sensor and is removable from the adhesive patch by the sensor inserter upon deployment of the physiological characteristic sensor.

Also provided is a system for a physiological characteristic sensor deployed with a sensor inserter. The system includes an adhesive patch coupled to the physiological characteristic sensor. The adhesive patch is to couple the physiological characteristic sensor to an anatomy. The system includes a gravity resistance system coupled to the adhesive patch and to the sensor inserter. The gravity resistance system includes at least one adhesive layer coupled between the adhesive patch and the sensor inserter. The at least one adhesive layer is coupled to a surface of the adhesive layer so as to be positioned about at least a portion of a perimeter of the adhesive patch. The gravity resistance system maintains the adhesive patch substantially perpendicular to a longitudinal axis of the sensor inserter prior to deployment of the physiological characteristic sensor and is removable from the adhesive patch by the sensor inserter upon deployment of the physiological characteristic sensor.

Further provided is a system for a physiological characteristic sensor deployed with a sensor inserter. The system includes an adhesive patch coupled to the physiological characteristic sensor. The adhesive patch is to couple the physiological characteristic sensor to an anatomy. The system includes a gravity resistance system coupled to the adhesive patch and to the sensor inserter. The gravity resistance system includes at least one adhesive layer coupled between the adhesive patch and the sensor inserter. The at least one adhesive layer is coupled to a surface of the adhesive layer so as to be positioned about a perimeter of the adhesive patch. The at least one adhesive layer comprises a first tack adhesive on a first side and a second tack adhesive on an opposite side, and the second tack adhesive is less tacky than the first tack adhesive. The gravity resistance system maintains the adhesive patch substantially perpendicular to a longitudinal axis of the sensor inserter prior to deployment of the physiological characteristic sensor and is removable from the adhesive patch by the sensor inserter upon deployment of the physiological characteristic sensor.

Also provided according to various embodiment is a system for a physiological characteristic sensor deployed with a sensor inserter. The system includes an adhesive patch coupled to the physiological characteristic sensor. The adhesive patch is to couple the physiological characteristic sensor to an anatomy. The system includes a gravity resistance system coupled to the adhesive patch and to be coupled to the sensor inserter. The gravity resistance system maintains the adhesive patch substantially perpendicular to a longitudinal axis of the sensor inserter prior to deployment of the physiological characteristic sensor and the gravity resistance system is to be removable from the sensor inserter by the adhesive patch upon deployment of the physiological characteristic sensor.

Further provided is a system for a physiological characteristic sensor deployed with a sensor inserter. The system includes an adhesive patch coupled to the physiological characteristic sensor. The adhesive patch is to couple the physiological characteristic sensor to an anatomy. The system includes a gravity resistance system coupled to the adhesive patch and the sensor inserter. The gravity resistance system comprises a low tack adhesive paper that has a first surface positioned opposite a second surface by a fold. The first surface is coupled to the adhesive patch and the second surface is coupled to the sensor inserter. The gravity resistance system maintains the adhesive patch substantially perpendicular to a longitudinal axis of the sensor inserter prior to deployment of the physiological characteristic sensor and the gravity resistance system is removable from the sensor inserter by the adhesive patch upon deployment of the physiological characteristic sensor.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 1 is a perspective view of an exemplary sensor introduction system that includes a sensor inserter and a physiological characteristic sensor assembly having an exemplary gravity resistance system according to various teachings of the present disclosure;

FIG. 2 is a cross-sectional view of the sensor introduction system of FIG. 1, taken along line 2-2 of FIG. 1;

DETAILED DESCRIPTION

Figure 3:
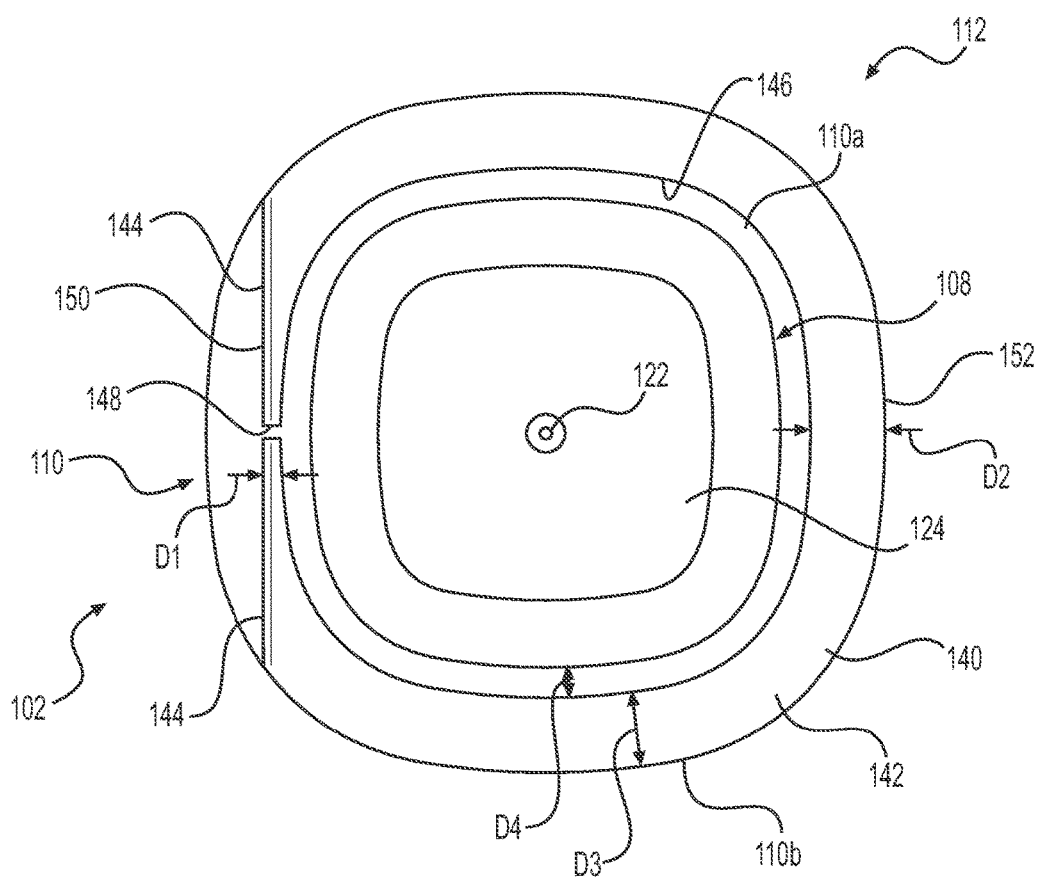
FIG. 3 is a top view of the physiological characteristic sensor assembly including the exemplary gravity resistance system of FIG. 1.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominantly in the respective nominal axial or radial direction. As used herein, the term "transverse" denotes an axis that crosses another axis at an angle such that the axis and the other axis are neither substantially perpendicular nor substantially parallel.

The following description relates to various embodiments of systems for adhesive skin patch gravity resistance. The systems described herein inhibit or mitigate the effects of gravity acting on an adhesive skin patch, during storage, for example, which ensures that the skin patch is properly adhered to a user. It should be noted that while the adhesive skin patch is described herein as being used with a glucose sensor, such as a glucose sensor associated with a continuous glucose monitor, it will be understood that the adhesive skin patch may be employed with a variety of other sensors, such as cardiac monitors, body temperature sensors, EKG monitors etc., medical devices, and/or other components that are intended to be affixed to the body of a user. Thus, while the non-limiting examples described below relate to a medical device used to treat diabetes (more specifically, an adhesive skin patch coupled to a continuous glucose monitor), embodiments of the disclosed subject matter are not so limited.

Generally, the glucose sensor employed with the adhesive patch is a continuous glucose sensor of the type used by diabetic users. For the sake of brevity, conventional aspects and technology related to glucose sensors and glucose sensor fabrication may not be described in detail here. In this regard, known and/or conventional aspects of glucose sensors and their manufacturing may be of the type described in, but not limited to: U.S. Pat. Nos. 6,892,085, 7,468,033 and 9,295,786; and United States patent application number 2009/0299301 (which are each incorporated by reference herein).

With reference to FIG. 1, FIG. 1 is a perspective view of a sensor introduction assembly 100. In one example, the sensor introduction assembly 100 includes a physiological characteristic sensor assembly 102 and a sensor inserter 104. It should be noted that in certain embodiments, the sensor inserter 104 and the physiological characteristic sensor 108 may comprise the insertion device and the sensor transmitter assembly described in commonly assigned U.S. Patent Publication No. 2017/0290533 to Antonio, et al., the relevant portion of which is incorporated herein by reference. In this example, with additional reference to FIG. 2, the physiological characteristic sensor assembly 102 includes a physiological characteristic sensor 108, an adhesive skin patch or adhesive patch 110 and a gravity resistance system 112. Generally, the components of the physiological characteristic sensor assembly 102 are coupled together as a single unit. The physiological characteristic sensor assembly 102 and the sensor inserter 104 may be packaged together for use by a consumer.

Certain features, aspects, and characteristics of the sensor inserter 104, the physiological characteristic sensor 108 and the adhesive patch 110 may be conventional and, as such, will not be described in detail here. Briefly, the physiological characteristic sensor 108 can be pre-connected as part of a sensor set, which could also include a sensor electronics module (not shown), such as a wireless transmitter that communicates with an infusion pump, a monitor device, or the like, which connects to the physiological characteristic sensor 108 after the insertion or deployment of a portion of the physiological characteristic sensor 108 in the body of the user. In one example, the physiological characteristic sensor 108 includes a glucose sensor 122 and a sensor base 124. It should be noted that the physiological characteristic sensor 108 is not limited to a glucose sensor, but rather, various other physiological characteristic sensors may be employed. The glucose sensor 122 may be provided as an integral part of the sensor base 124. The sensor base 124 gives structural support to the glucose sensor 122, and facilitates entry of the glucose sensor 122 into the body of the user. The glucose sensor 122 is an electrochemical sensor that includes the glucose oxidase enzyme, as is well understood by those familiar with glucose sensor technology. The glucose oxidase enzyme enables the glucose sensor 122 to monitor blood glucose levels in a diabetic patient or user by effecting a reaction of glucose and oxygen. Again, although certain embodiments pertain to glucose sensors, the technology described here can be adapted for use with any one of the wide variety of sensors known in the art. Generally, the glucose sensor 122 is positionable in subcutaneous tissue of the user by an insertion needle 126 of the sensor inserter 104 to measure the glucose oxidase enzyme.

The sensor base 124 is coupled to the sensor inserter 104 and is coupled to the adhesive patch 110. The sensor base 124 is removably coupled to the sensor inserter 104. The sensor base 124 may also feature electrical and physical interfaces and elements that accommodate the sensor electronics module, such as the wireless transmitter that communicates with the infusion pump, the monitor device, or the like. In certain embodiments the sensor base 124 is composed at least in part from a plastic material. For the embodiment described here, the bulk of the sensor base 124 is formed as a molded plastic component. In one example, the sensor base 124 is formed from acrylonitrile butadiene styrene, nylon, an acrylonitrile butadiene styrene polycarbonate blend, polyvinyl chloride, polytetrafluoroethylene (PTFE), polypropylene, polyether ether ketone (PEEK), polycarbonate or the like.

The adhesive patch 110 is coupled to the sensor base 124 and affixes the sensor base 124, and thus, the glucose sensor 122, to an anatomy, such as the skin of the user. The adhesive patch 110 is contained within the sensor inserter 104 during packaging and shipping, and is exposed to the force of gravity G. The adhesive patch 110 may be composed of a flexible and breathable material with one or more adhesive layers, such as cloth, a bandage-like material, and the like. For example, suitable materials could include polyurethane, polyethylene, polyester, polypropylene, polytetrafluoroethylene (PTFE), or other polymers, to which one or more adhesive layers are applied.

The sensor inserter 104 is coupled to the physiological characteristic sensor 108 and is manipulatable by a user to couple the glucose sensor 122 to the user. With continued reference to FIG. 2, the sensor inserter 104 includes a housing 130, a cradle or monitor support 132, one or more biasing members or springs 134 and a lid or cover 136. In one example, the housing 130 surrounds the physiological characteristic sensor assembly 102 and encloses the physiological characteristic sensor assembly 102 to enable sterilization of the physiological characteristic sensor assembly 102, for example. The housing 130 may include one or more features, such as movable tabs, that cooperate with the monitor support 132 to deploy the physiological characteristic sensor 108 into the anatomy. The monitor support 132 is coupled to the physiological characteristic sensor 108, and is movable relative to the housing 130 to deploy the physiological characteristic sensor 108 into the anatomy. For example, the application of a force to the housing 130 may bias the tabs to release the monitor support 132 to enable a spring 134 associated with the monitor support 132 to drive the monitor support 132 to deploy the physiological characteristic sensor 108 into the anatomy. Once released, another spring 134b cooperates with the monitor support 132 to move a needle retractor 131 relative to the housing 130. The cover 136 surrounds a circumferentially open end of the housing 130, and encloses the housing 130. Generally, the cover 136 is coupled to the housing 130 such that the adhesive patch 110 is unsupported by the cover 136. As will be discussed, the gravity resistance system 112 inhibits or mitigates the force of gravity G from pulling down on the unsupported adhesive patch 110, which in turn, inhibits or mitigates the drooping or sagging of the adhesive patch 110 within the sensor inserter 104 ensuring full contact is made between an entirety of the adhesive patch 110 and the anatomy of the user.

Figure 4:
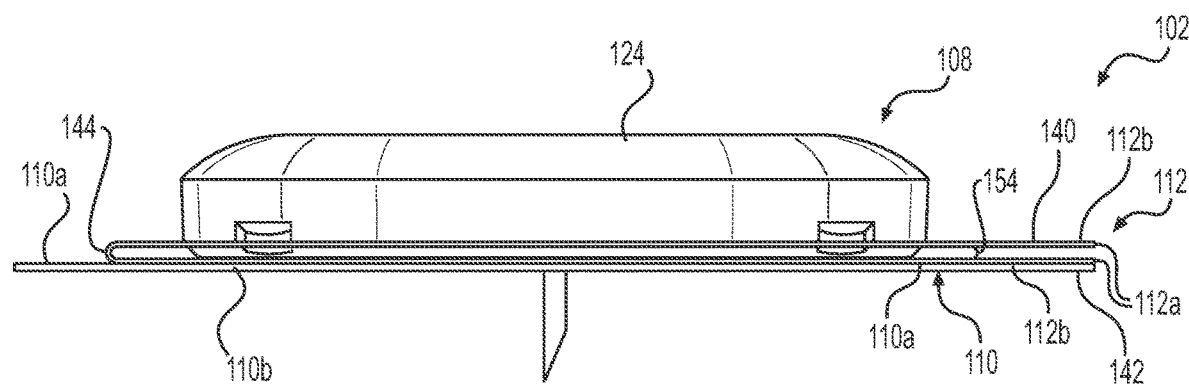
FIG. 4 is a side view of the physiological characteristic sensor assembly including the exemplary gravity resistance system of FIG. 1.

In one example, with reference to FIG. 3, the gravity resistance system 112 is shown in greater detail. FIG. 3 is a top view of the physiological characteristic sensor assembly 102, which illustrates the gravity resistance system 112 coupled to the adhesive patch 110. In this example, the gravity resistance system 112 is a low tack adhesive cast paper, which is coupled to the adhesive patch 110 and the monitor support 132 (FIG. 2). The gravity resistance system 112 includes a first, top surface 140 and a second, bottom surface 142, which are interconnected at a fold 144 (FIG. 4). The gravity resistance system 112 is substantially annular, and defines an aperture 146, which is sized to enable the gravity resistance system 112 to be positioned about a perimeter of the sensor base 124. Generally, the gravity resistance system 112 surrounds an entirety of a circumference of the sensor base 124, and may include a slit 148. The slit 148 enables the removal of the gravity resistance system 112 from the adhesive patch 110, if desired, by the user once the physiological characteristic sensor 108 is coupled to the anatomy. In this example, the slit 148 is defined at an end 150 of the gravity resistance system 112 that includes the fold 144. The fold 144 may be configured such that the end 150 extends for a distance D1, which is different and less than a distance D2 of an opposed end 152 of the gravity resistance system 112. In this example, the gravity resistance system 112 is coupled to a surface 110a of the adhesive patch 110 along a perimeter 110b of the adhesive patch 110, and extends for a distance D3 from the perimeter of the adhesive patch 110 toward the sensor base 124. Generally, the gravity resistance system 112 is spaced apart from the sensor base 124 by a fourth distance D4, which is different and less than the distance D3.

In this example, with reference to FIG. 4, the gravity resistance system 112 is composed of a base layer 112a to which a low tack adhesive 112b is applied. Generally, the low tack adhesive 112b is only applied to a single surface of the base layer 112a, so that when folded, the top surface 140 and the bottom surface 142 include the low tack adhesive 112b, but facing surfaces 154 remain uncoated with the low tack adhesive 112b. In one example, the base layer 112a is composed of paper, poly-coated paper, polymers such as polyester film or HDPE film, etc.; and the low tack adhesive 112b is composed of silicone, acrylic, etc. The low tack adhesive 112b may be cast, coated, painted or otherwise coupled to the base layer 112a. The low tack adhesive 112b along the bottom surface 142 is coupled or adhered to the surface 110a of the adhesive patch 110, while the low tack adhesive 112b along the top surface 140 is coupled or adhered to a surface 132a of the monitor support 132 (FIG. 2). As used herein, a "low tack" adhesive is an adhesive that has a bond weak enough to enable easy separation of the adhesive in its intended use (such as, separation of the liner from the adhesive patch either before or after insertion). As used herein, "high tack" adhesive is an adhesive in which the bond is intended to be permanent (i.e. no separation). For example, as used herein, a "low tack" adhesive has about 0.5 ounce per inch (oz/in.) to about 5 ounce per inch (oz/in.) peel force adhesion to stainless steel per ASTM D6862-11 Standard Test Method for 90 Degree Peel Resistance of Adhesives, and a "high tack" adhesive has greater than 5 ounce per inch (oz/in.) peel force adhesion to stainless steel per ASTM D6862-11 Standard Test Method for 90 Degree Peel Resistance of Adhesives.

In one example, with the physiological characteristic sensor 108 assembled and coupled to the adhesive patch 110 and the gravity resistance system 112 formed, the low tack adhesive 112b on the bottom surface 142 is coupled to the adhesive patch 110 so as to surround the sensor base 124. The top surface 140 is folded at the fold 144 over the bottom surface 142. With the physiological characteristic sensor assembly 102 assembled, and the springs 134 and the monitor support 132 coupled to the housing 130, with reference to FIG. 3, the physiological characteristic sensor assembly 102 is coupled to the sensor inserter 104 such that the low tack adhesive 112b is coupled to the surface 132a of the monitor support 132. With the physiological characteristic sensor assembly 102 coupled to the monitor support 132, the cover 136 is coupled to the housing 130 to enclose the physiological characteristic sensor assembly 102. The sensor inserter 104, including the physiological characteristic sensor assembly 102, may be sterilized and shipped to an end user.

Once received, the user may remove the cover 136 to expose the physiological characteristic sensor assembly 102. The user may manipulate the sensor inserter 104 to deploy the physiological characteristic sensor assembly 102 onto the user. Once deployed, the low tack adhesive 112b on the top surface 140 enables the removal of the sensor inserter 104 from the physiological characteristic sensor assembly 102 without uncoupling the adhesive patch 110 from the user. With the sensor inserter 104 uncoupled from the physiological characteristic sensor assembly 102 and the physiological characteristic sensor assembly 102 deployed on the user, the user may pull the top surface 140 of the gravity resistance system 112 to remove the gravity resistance system 112 from the adhesive patch 110, if desired.

By providing the low tack adhesive 112b on the top surface 140, the sensor inserter 104 is removable from the physiological characteristic sensor 108 upon deployment without removing the adhesive patch 110 from the user. Thus, the gravity resistance system 112 is removable from the sensor inserter 104 by the adhesive patch 110 upon deployment of the physiological characteristic sensor 108.

In addition, the low tack adhesive 112b on the bottom surface 142 allows for the use of larger adhesive patches 110, while inhibiting the drooping of the adhesive patch 110. In this regard, the gravity resistance system 112 adds structure and rigidity to the portion of the adhesive patch 110 that extends beyond the sensor base 124 (FIG. 3). Stated another way, the gravity resistance system 112 maintains the adhesive patch 110 substantially perpendicular to a longitudinal axis LA1 of the sensor inserter 104, which ensures the adhesive patch 110, when deployed, is properly coupled to the user. The fold 144 also allows for removal of the gravity resistance system 112 by the user upon deployment, if desired.

Figure 5:
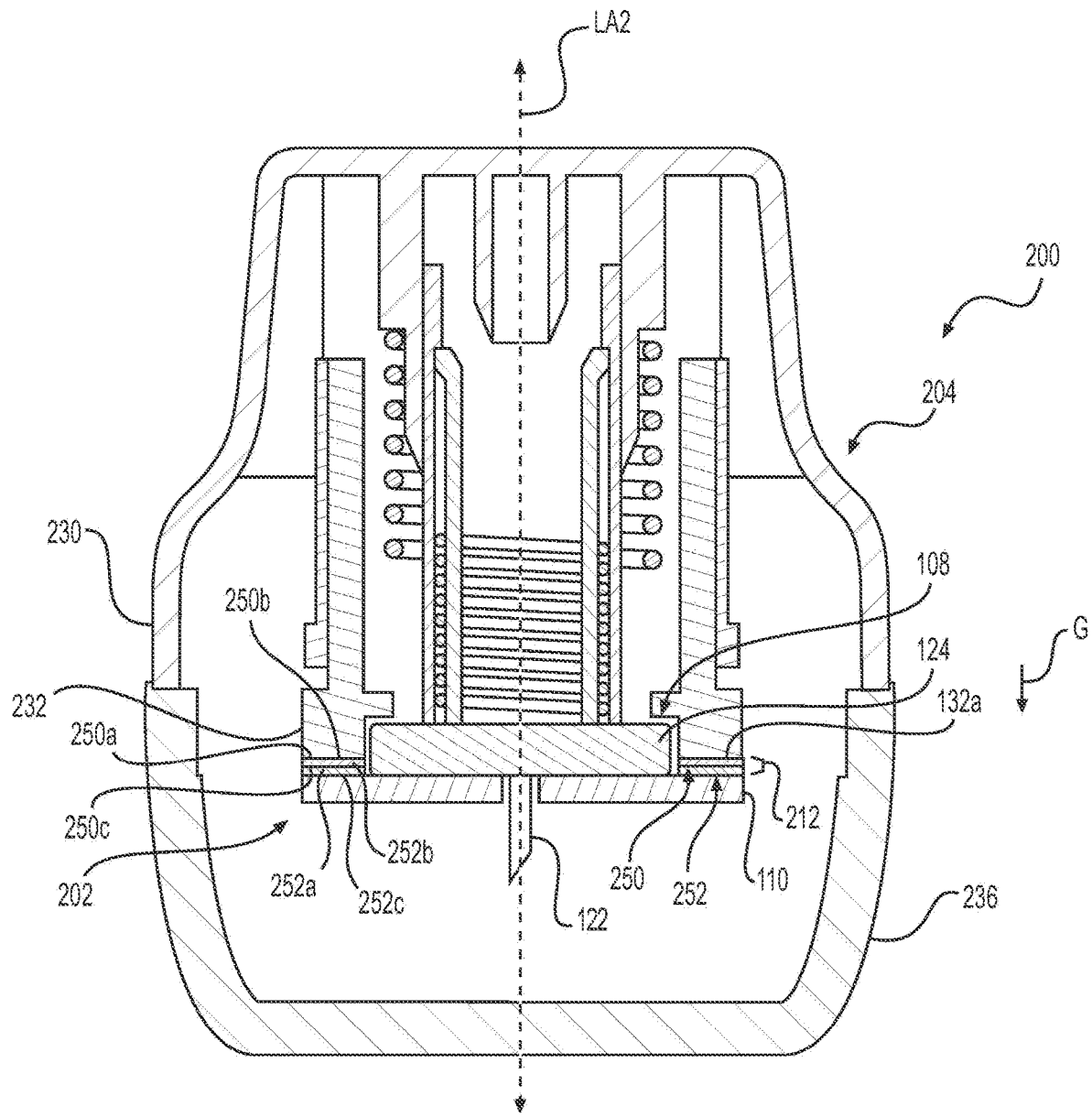
FIG. 5 is a cross-sectional view of another exemplary sensor introduction system that includes a sensor inserter and a physiological characteristic sensor assembly having an exemplary gravity resistance system according to various teachings of the present disclosure, taken from the perspective of line 2-2 of FIG. 1.

It should be noted that in other embodiments, the gravity resistance system 112 may be configured differently to inhibit or mitigate the effects of gravity on the adhesive patch 110. For example, with reference to FIG. 5, a sensor introduction assembly 200 is shown. As the sensor introduction assembly 200 includes the same or similar components as the sensor introduction assembly 100 discussed with regard to FIGS. 1-4, the same reference numerals will be used to denote the same or similar components. FIG. 5 is a schematic cross-sectional view, taken from the perspective of line 2-2 of FIG. 1. In this example, the sensor introduction assembly 200 includes a physiological characteristic sensor assembly 202 and a sensor inserter 204. In this example, the physiological characteristic sensor assembly 202 includes the physiological characteristic sensor 108, the adhesive patch 110 and a gravity resistance system 212. Generally, the components of the physiological characteristic sensor assembly 102 are coupled together as a single unit. The physiological characteristic sensor assembly 202 and the sensor inserter 204 may be packaged together for use by a consumer.

The physiological characteristic sensor 108 includes the glucose sensor 122 and the sensor base 124. Generally, the glucose sensor 122 is positionable in subcutaneous tissue of the user by an insertion needle of the sensor inserter 204 to measure the glucose oxidase enzyme. The sensor base 124 is coupled to the sensor inserter 204 and is coupled to the adhesive patch 110. The sensor base 124 is removably coupled to the sensor inserter 204. The adhesive patch 110 is coupled to the sensor base 124 and affixes the sensor base 124, and thus, the glucose sensor 122, to the skin of the user. The adhesive patch 110 is contained within the sensor inserter 204 during packaging and shipping, and is exposed to the force of gravity G.

The sensor inserter 204 is coupled to the physiological characteristic sensor 108 and is manipulatable by a user to couple the glucose sensor 122 to the user. Briefly, the sensor inserter 204 includes a housing 230, a monitor support 232 and a lid or cover 236. In one example, the housing 230 surrounds the physiological characteristic sensor assembly 202 and encloses the physiological characteristic sensor assembly 202 to enable sterilization of the physiological characteristic sensor assembly 202, for example. The housing 230 may include one or more features that cooperate with the monitor support 232 to deploy the physiological characteristic sensor 108 into the anatomy. The monitor support 232 is coupled to the physiological characteristic sensor 108, and is manipulated by the user to deploy the physiological characteristic sensor 108. The cover 236 surrounds a circumferentially open end of the housing 230, and encloses the housing 230. Generally, the cover 236 is coupled to the housing 230 such that the adhesive patch 110 is unsupported by the cover 236. As will be discussed, the gravity resistance system 212 inhibits or mitigates the force of gravity G from pulling down on the unsupported adhesive patch 110, which in turn, inhibits or mitigates the drooping or sagging of the adhesive patch 110 within the sensor inserter 104 ensuring full contact is made between an entirety of the adhesive patch 110 and the anatomy of the user.

Figure 6:
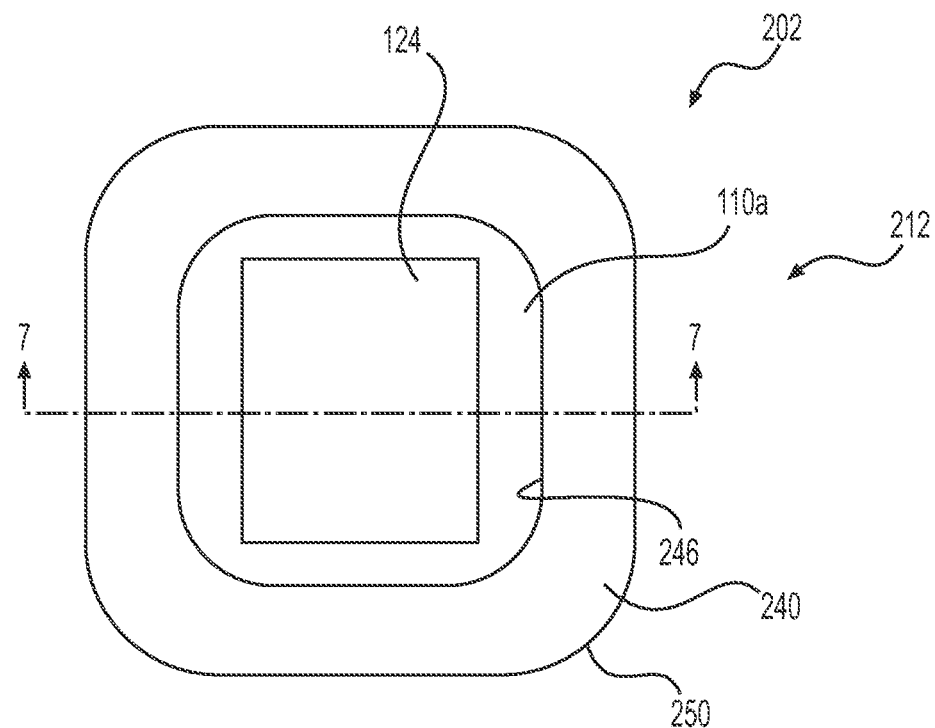
FIG. 6 is a top view of the physiological characteristic sensor assembly including the exemplary gravity resistance system of FIG. 5.
Figure 7:
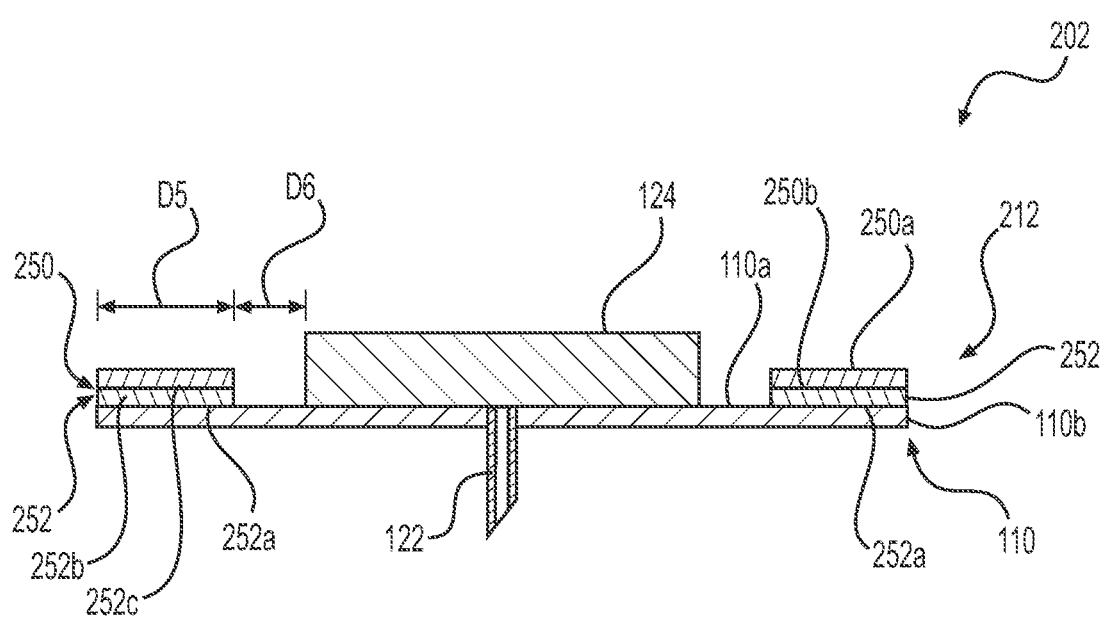
FIG. 7 is a cross-sectional view of the physiological characteristic sensor assembly including the exemplary gravity resistance system of FIG. 6, taken along line 7-7 of FIG. 6.
Figure 8:
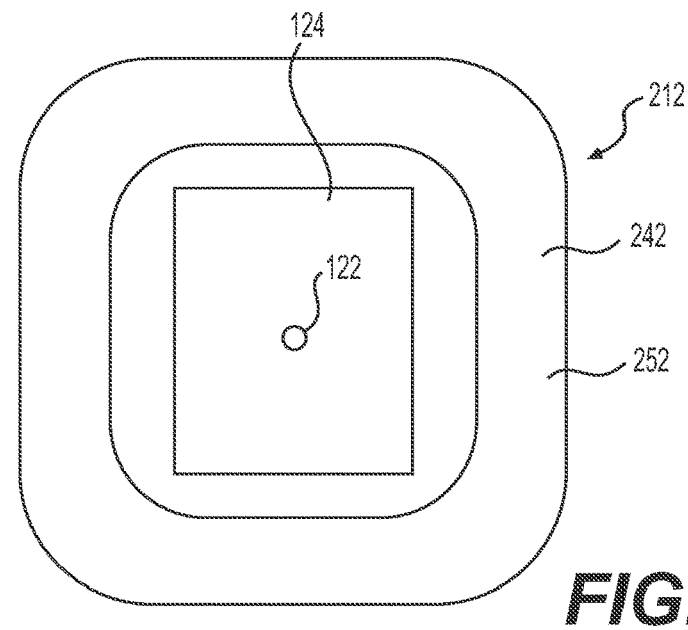
FIG. 8 is a bottom view of the physiological characteristic sensor assembly including the exemplary gravity resistance system of FIG. 5, in which an adhesive patch associated with the physiological characteristic sensor assembly is removed for clarity.

In one example, with reference to FIG. 6, the gravity resistance system 212 is shown in greater detail. FIG. 6 is a top view of the physiological characteristic sensor assembly 202, which illustrates the gravity resistance system 212 coupled to the adhesive patch 110. With reference to FIGS. 6 and 8, the gravity resistance system 212 includes a first, top surface 240 and a second, bottom surface 242 (FIG. 8). In FIG. 8, the adhesive patch 110 is removed for clarity. The gravity resistance system 212 is substantially annular, and defines an aperture 246, which is sized to enable the gravity resistance system 212 to be positioned about a perimeter of the sensor base 124. Generally, the gravity resistance system 212 surrounds an entirety of a circumference of the sensor base 124. In this example, with reference to FIG. 7, the gravity resistance system 212 is coupled to the surface 110a of the adhesive patch 110 along the perimeter 110b of the adhesive patch 110, and extends for a distance D5 from the perimeter of the adhesive patch 110 toward the sensor base 124. Generally, the gravity resistance system 212 is spaced apart from the sensor base 124 by a sixth distance D6, which is different and less than the distance D5.

In this example, the gravity resistance system 212 is a double sided differential adhesive, which includes a high tack adhesive layer 250 coupled to a low tack adhesive layer 252. The high tack adhesive layer 250 is coupled to the monitor support 232 (FIG. 5), and the low tack adhesive layer 252 is coupled to the adhesive patch 110. In this example, high tack adhesive 250a is coupled to or formed on opposed sides of a base layer. The base layer is composed of paper, poly-coated paper, polymers such as polyester film or HDPE film, etc. The top surface 240 of the gravity resistance system 212 is defined by one side 250b of the high tack adhesive layer 250, which is coupled to or formed on the base layer. In one example, the high tack adhesive 250a is composed of silicone, acrylic, etc. The high tack adhesive 250a may be cast, coated, painted or otherwise coupled to the base layer. The opposed side 250c of the high tack adhesive layer 250 formed on the base layer is coupled or adhered to the low tack adhesive layer 252.

In this example, low tack adhesive 252a is coupled to or formed on opposed sides of a second base layer. The bottom surface 242 of the gravity resistance system 212 is defined by one side 252b of the low tack adhesive layer 252, which is coupled to or formed on the second base layer. The second base layer is composed of paper, poly-coated paper, polymers such as polyester film or HDPE film. In one example, the low tack adhesive 252a is composed of silicone, acrylic, etc. The low tack adhesive 252a may be cast, coated, painted or otherwise coupled to the second base layer. The opposed side 252c of low tack adhesive layer 252 formed on the second base layer is coupled or adhered to the side 250c of the high tack adhesive layer 250 to form the gravity resistance system 212. Thus, the high tack adhesive 250a is a first tack adhesive, and the low tack adhesive 252a is a second tack adhesive, with the second tack adhesive different and less than the first tack adhesive. It should be noted that for ease of illustration, the base layer and the second base layer are not shown in the drawings as these paper or film layers have a predetermined nominal thickness.

In one example, with the physiological characteristic sensor 108 assembled and coupled to the adhesive patch 110 and the gravity resistance system 212 formed, with reference to FIG. 5, the low tack adhesive layer 252 on the bottom surface 242 is coupled to the adhesive patch 110 so as to surround the sensor base 124. With the physiological characteristic sensor assembly 202 assembled and the monitor support 232 coupled to the housing 230, the physiological characteristic sensor assembly 202 is coupled to the sensor inserter 204 such that the high tack adhesive layer 250 is coupled to the surface 232a of the monitor support 232. With the physiological characteristic sensor assembly 202 coupled to the monitor support 232, the cover 236 is coupled to the housing 230 to enclose the physiological characteristic sensor assembly 202. The sensor inserter 204, including the physiological characteristic sensor assembly 202, may be sterilized and shipped to an end user.

Once received, the user may remove the cover 236 to expose the physiological characteristic sensor assembly 202. The user may manipulate the sensor inserter 204 to deploy the physiological characteristic sensor assembly 202 onto the user. Once deployed, the high tack adhesive layer 250 on the top surface 240 retains the gravity resistance system 212 on the sensor inserter 204, and the low tack adhesive layer 252 enables the removal of the gravity resistance system 212 from the adhesive patch 110 without uncoupling the adhesive patch 110 from the user. Thus, the gravity resistance system 212 is removable from the adhesive patch 110 by the sensor inserter 204 upon deployment of the physiological characteristic sensor 108. The differential adhesive of the gravity resistance system 212 enables the sensor inserter 204 to be uncoupled from the physiological characteristic sensor 108 when the physiological characteristic sensor 108 is coupled to the user with the adhesive patch 110 without uncoupling the physiological characteristic sensor 108 and the adhesive patch 110 from the user.

By providing the high tack adhesive layer 250 on the top surface 240 and the low tack adhesive layer 252 on the bottom surface 242, the gravity resistance system 212 is retained on the sensor inserter 204 and is removable from the physiological characteristic sensor 108 upon deployment without removing the adhesive patch 110 from the user. In addition, the low tack adhesive layer 252 on the bottom surface 242 allows for the use of larger adhesive patches 110, while inhibiting the drooping of the adhesive patch 110. In this regard, the gravity resistance system 212 adds structure and rigidity to the portion of the adhesive patch 110 that extends beyond the sensor base 124. Stated another way, the gravity resistance system 212 maintains the adhesive patch 110 substantially perpendicular to a longitudinal axis LA2 of the sensor inserter 204, which ensures the adhesive patch 110, when deployed, is properly coupled to the user.

Figure 9:
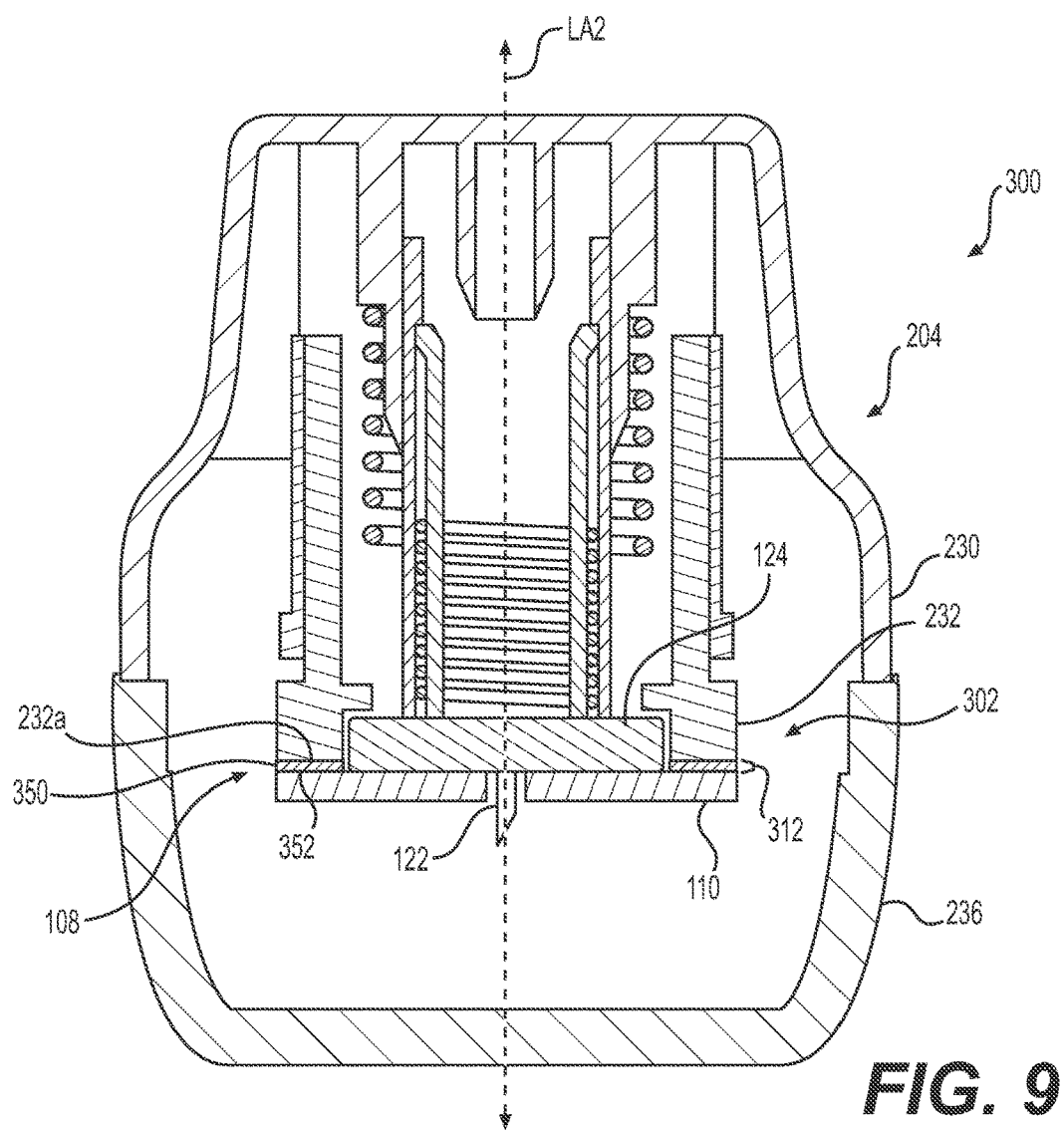
FIG. 9 is a cross-sectional view of another exemplary sensor introduction system that includes a sensor inserter and a physiological characteristic sensor assembly having an exemplary gravity resistance system according to various teachings of the present disclosure, taken from the perspective of line 2-2 of FIG. 1.

It should be noted that in other embodiments, the gravity resistance system 112 may be configured differently to inhibit or mitigate the effects of gravity on the adhesive patch 110. For example, with reference to FIG. 9, a sensor introduction assembly 300 is shown. As the sensor introduction assembly 300 includes the same or similar components as the sensor introduction assembly 100 discussed with regard to FIGS. 1-4 and the sensor introduction assembly 200 discussed with regard to FIGS. 5-8, the same reference numerals will be used to denote the same or similar components. FIG. 9 is a schematic cross-sectional view, taken from the perspective of line 2-2 of FIG. 1. In this example, the sensor introduction assembly 300 includes a physiological characteristic sensor assembly 302 and the sensor inserter 204. In this example, the physiological characteristic sensor assembly 302 includes the physiological characteristic sensor 108, the adhesive patch 110 and a gravity resistance system 312. Generally, the components of the physiological characteristic sensor assembly 302 are coupled together as a single unit. The physiological characteristic sensor assembly 302 and the sensor inserter 204 may be packaged together for use by a consumer.

The physiological characteristic sensor 108 includes the glucose sensor 122 and the sensor base 124. The sensor base 124 is coupled to the sensor inserter 204 and is coupled to the adhesive patch 110. The sensor base 124 is removably coupled to the sensor inserter 204. The adhesive patch 110 is coupled to the sensor base 124 and affixes the sensor base 124, and thus, the glucose sensor 122, to the skin of the user. The adhesive patch 110 is contained within the sensor inserter 204 during packaging and shipping, and is exposed to the force of gravity G.

The sensor inserter 204 is coupled to the physiological characteristic sensor 108 and is manipulatable by a user to couple the glucose sensor 122 to the user. Briefly, the sensor inserter 204 includes the housing 230, the monitor support 232 and the lid or cover 236. In one example, the housing 230 surrounds the physiological characteristic sensor assembly 302 and encloses the physiological characteristic sensor assembly 302 to enable sterilization of the physiological characteristic sensor assembly 302, for example. The housing 230 may include one or more features that cooperate with the monitor support 232 to deploy the physiological characteristic sensor 108 into the anatomy. The monitor support 232 is coupled to the physiological characteristic sensor 108, and is manipulated by the user to deploy the physiological characteristic sensor 108. The cover 236 surrounds the circumferentially open end of the housing 230, and encloses the housing 230. Generally, the cover 236 is coupled to the housing 230 such that the adhesive patch 110 is unsupported by the cover 236. As will be discussed, the gravity resistance system 312 inhibits or mitigates the force of gravity G from pulling down on the unsupported adhesive patch 110, which in turn, inhibits or mitigates the drooping or sagging of the adhesive patch 110 within the sensor inserter 204 ensuring full contact is made between an entirety of the adhesive patch 110 and the anatomy of the user.

Figure 10:
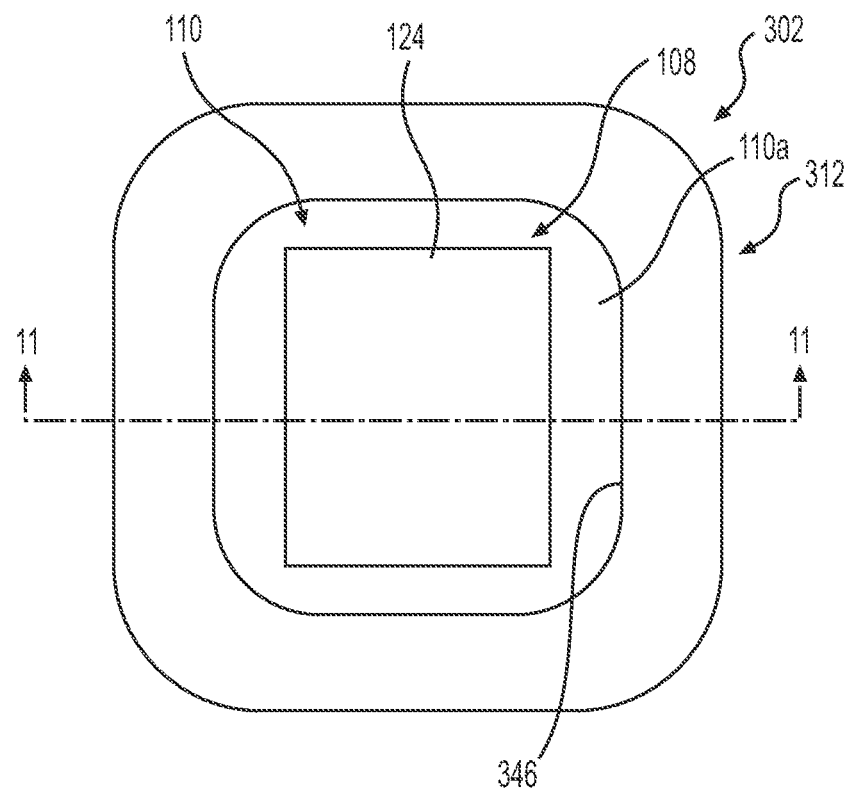
FIG. 10 is a top view of the physiological characteristic sensor assembly including the exemplary gravity resistance system of FIG. 9.
Figure 11:
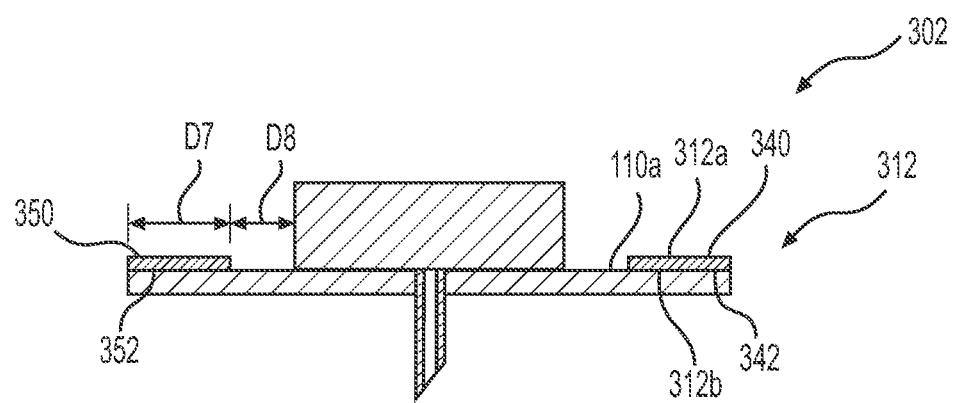
FIG. 11 is a cross-sectional view of the physiological characteristic sensor assembly including the exemplary gravity resistance system of FIG. 10, taken along line 11-11 of FIG. 10.

In one example, with reference to FIG. 10, the gravity resistance system 312 is shown in greater detail. FIG. 10 is a top view of the physiological characteristic sensor assembly 302, which illustrates the gravity resistance system 312 coupled to the adhesive patch 110. With reference to FIGS. 10 and 11, the gravity resistance system 312 includes a first, top surface 340 and a second, bottom surface 342 (FIG. 11). The gravity resistance system 312 is substantially annular, and defines an aperture 346, which is sized to enable the gravity resistance system 312 to be positioned about a perimeter of the sensor base 124 (FIG. 10). Generally, the gravity resistance system 312 surrounds an entirety of a circumference of the sensor base 124. In this example, with reference to FIG. 11, the gravity resistance system 312 is coupled to the surface 110a of the adhesive patch 110 along the perimeter 110b of the adhesive patch 110, and extends for a distance D7 from the perimeter of the adhesive patch 110 toward the sensor base 124. Generally, the gravity resistance system 312 is spaced apart from the sensor base 124 by an eighth distance D8, which is different and less than the distance D7.

In this example, the gravity resistance system 312 is a single layer double sided differential adhesive, which includes a high tack adhesive 350 on a first side 312a and a low tack adhesive 352 on a second side 312b. The high tack adhesive 350 is coupled to the monitor support 332 (FIG. 9), and the low tack adhesive 352 is coupled to the adhesive patch 110. In this example, high tack adhesive 350 and the low tack adhesive 352 are each coupled to or formed on opposed sides of a base layer. The base layer is composed of paper, poly-coated paper, polymers such as polyester film or HDPE film. The top surface 340 of the gravity resistance system 312 is defined by the high tack adhesive 350 and the bottom surface 342 of the gravity resistance system 312 is defined by the low tack adhesive 352, which are coupled to or formed on opposed sides of the base layer. In one example, the high tack adhesive 350 is composed of synthetic rubber adhesives, acrylic, etc. The high tack adhesive 350 may be cast, coated, painted or otherwise coupled to the base layer. The low tack adhesive 352 is coupled to or formed on a second, opposed side of the base layer. In one example, the low tack adhesive 352 is composed of silicone, acrylic, etc. The low tack adhesive 352 may be cast, coated, painted or otherwise coupled to the base layer. It should be noted that for ease of illustration, the base layer is not shown in the drawings as this paper or film layer has a predetermined nominal thickness.

In one example, with the physiological characteristic sensor 108 assembled and coupled to the adhesive patch 110 and the gravity resistance system 312 formed, with reference to FIG. 9, the low tack adhesive 352 on the bottom surface 342 is coupled to the adhesive patch 110 so as to surround the sensor base 124. With the physiological characteristic sensor assembly 302 assembled and the monitor support 232 coupled to the housing 230, the physiological characteristic sensor assembly 302 is coupled to the sensor inserter 204 such that the high tack adhesive 350 is coupled to the surface 232a of the monitor support 232. With the physiological characteristic sensor assembly 302 coupled to the monitor support 232, the cover 236 is coupled to the housing 230 to enclose the physiological characteristic sensor assembly 302. The sensor inserter 204, including the physiological characteristic sensor assembly 302, may be sterilized and shipped to an end user.

Once received, the user may remove the cover 236 to expose the physiological characteristic sensor assembly 302. The user may manipulate the sensor inserter 204 to deploy the physiological characteristic sensor assembly 302 onto the user. Once deployed, the high tack adhesive 350 on the top surface 340 retains the gravity resistance system 312 on the sensor inserter 204, and the low tack adhesive 352 enables the removal of the gravity resistance system 312 from the adhesive patch 110 without uncoupling the adhesive patch 110 from the user. Thus, the differential adhesive of the gravity resistance system 312 enables the sensor inserter 204 to be uncoupled from the physiological characteristic sensor 108 when the physiological characteristic sensor 108 is coupled to the user with the adhesive patch 110 without uncoupling the physiological characteristic sensor 108 and the adhesive patch 110 from the user.

By providing the high tack adhesive 350 on the top surface 340 and the low tack adhesive 352 on the bottom surface 342, the gravity resistance system 312 is retained on the sensor inserter 204 and is removable from the physiological characteristic sensor 108 upon deployment without removing the adhesive patch 110 from the user. Thus, the gravity resistance system 312 is removable from the adhesive patch 110 by the sensor inserter 204 upon deployment of the physiological characteristic sensor 108. In addition, the low tack adhesive 352 on the bottom surface 342 allows for the use of larger adhesive patches 110, while inhibiting the drooping of the adhesive patch 110. In this regard, the gravity resistance system 312 adds structure and rigidity to the portion of the adhesive patch 110 that extends beyond the sensor base 124. Stated another way, the gravity resistance system 312 maintains the adhesive patch 110 substantially perpendicular to the longitudinal axis LA2 of the sensor inserter 204, which ensures the adhesive patch 110, when deployed, is properly coupled to the user.

Figure 12:
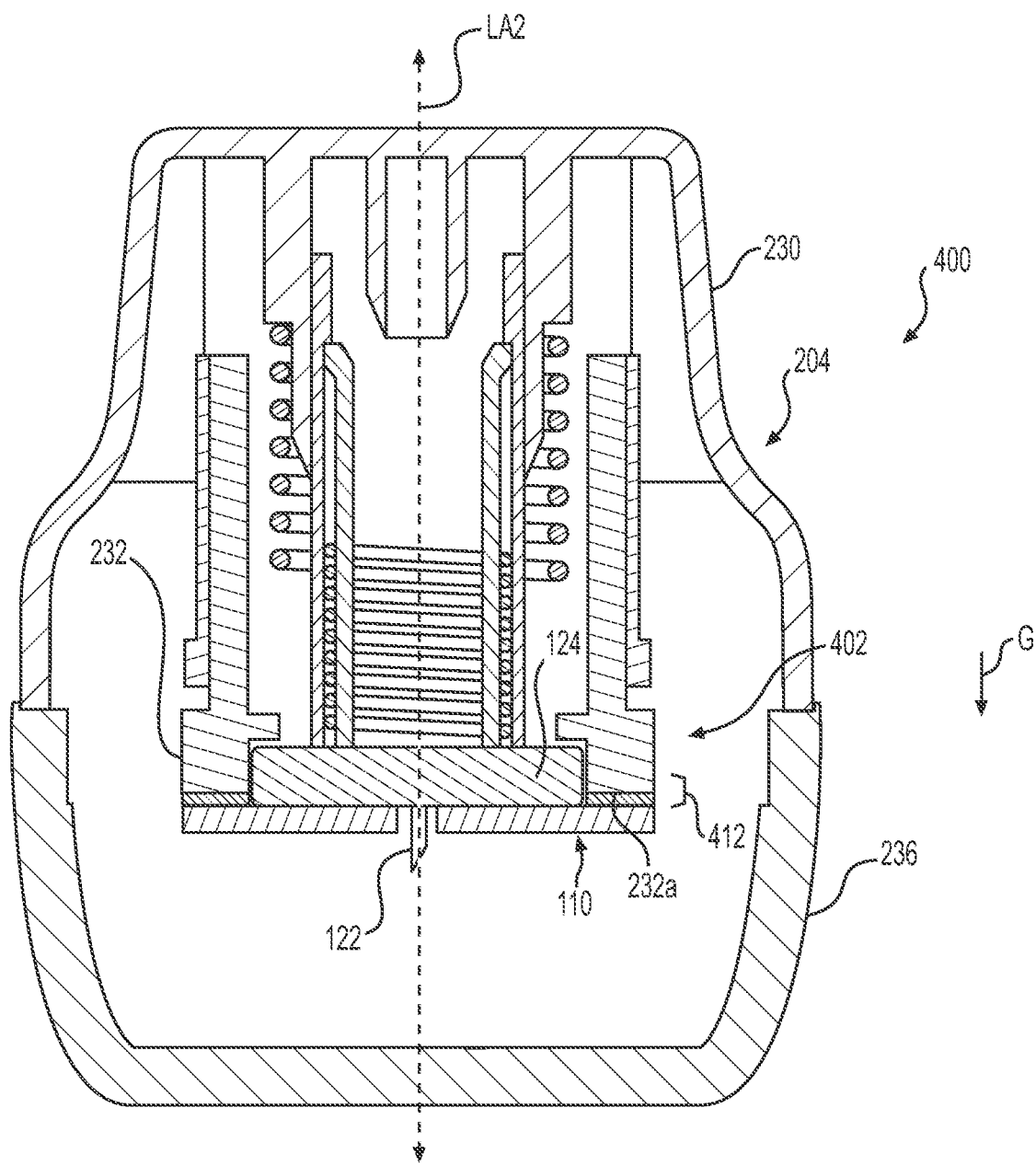
FIG. 12 is a cross-sectional view of another exemplary sensor introduction system that includes a sensor inserter and a physiological characteristic sensor assembly having an exemplary gravity resistance system according to various teachings of the present disclosure, taken from the perspective of line 2-2 of FIG. 1.

It should be noted that in other embodiments, the gravity resistance system 112 may be configured differently to inhibit or mitigate the effects of gravity on the adhesive patch 110. For example, with reference to FIG. 12, a sensor introduction assembly 400 is shown. As the sensor introduction assembly 400 includes the same or similar components as the sensor introduction assembly 100 discussed with regard to FIGS. 1-4 and the sensor introduction assembly 200 discussed with regard to FIGS. 5-8, the same reference numerals will be used to denote the same or similar components. FIG. 12 is a schematic cross-sectional view, taken from the perspective of line 2-2 of FIG. 1. In this example, the sensor introduction assembly 400 includes a physiological characteristic sensor assembly 402 and the sensor inserter 204. In this example, the physiological characteristic sensor assembly 402 includes the physiological characteristic sensor 108, the adhesive patch 110 and a gravity resistance system 412. Generally, the components of the physiological characteristic sensor assembly 402 are coupled together as a single unit. The physiological characteristic sensor assembly 402 and the sensor inserter 204 may be packaged together for use by a consumer.

The physiological characteristic sensor 108 includes the glucose sensor 122 and the sensor base 124. The sensor base 124 is coupled to the sensor inserter 204 and is coupled to the adhesive patch 110. The sensor base 124 is removably coupled to the sensor inserter 204. The adhesive patch 110 is coupled to the sensor base 124 and affixes the sensor base 124, and thus, the glucose sensor 122, to the skin of the user. The adhesive patch 110 is contained within the sensor inserter 204 during packaging and shipping, and is exposed to the force of gravity G.

The sensor inserter 204 is coupled to the physiological characteristic sensor 108 and is manipulatable by a user to couple the glucose sensor 122 to the user. Briefly, the sensor inserter 204 includes the housing 230, the monitor support 232 and the lid or cover 236. In one example, the housing 230 surrounds the physiological characteristic sensor assembly 202 and encloses the physiological characteristic sensor assembly 202 to enable sterilization of the physiological characteristic sensor assembly 202, for example. The housing 230 may include one or more features that cooperate with the monitor support 232 to deploy the physiological characteristic sensor 108 into the anatomy. The monitor support 232 is coupled to the physiological characteristic sensor 108, and is manipulated by the user to deploy the physiological characteristic sensor 108 into the anatomy. The cover 236 surrounds the circumferentially open end of the housing 230, and encloses the housing 230. Generally, the cover 236 is coupled to the housing 230 such that the adhesive patch 110 is unsupported by the cover 236. As will be discussed, the gravity resistance system 412 inhibits or mitigates the force of gravity G from pulling down on the unsupported adhesive patch 110, which in turn, inhibits or mitigates the drooping or sagging of the adhesive patch 110 within the sensor inserter 204 ensuring full contact is made between an entirety of the adhesive patch 110 and the anatomy of the user.

Figure 13:
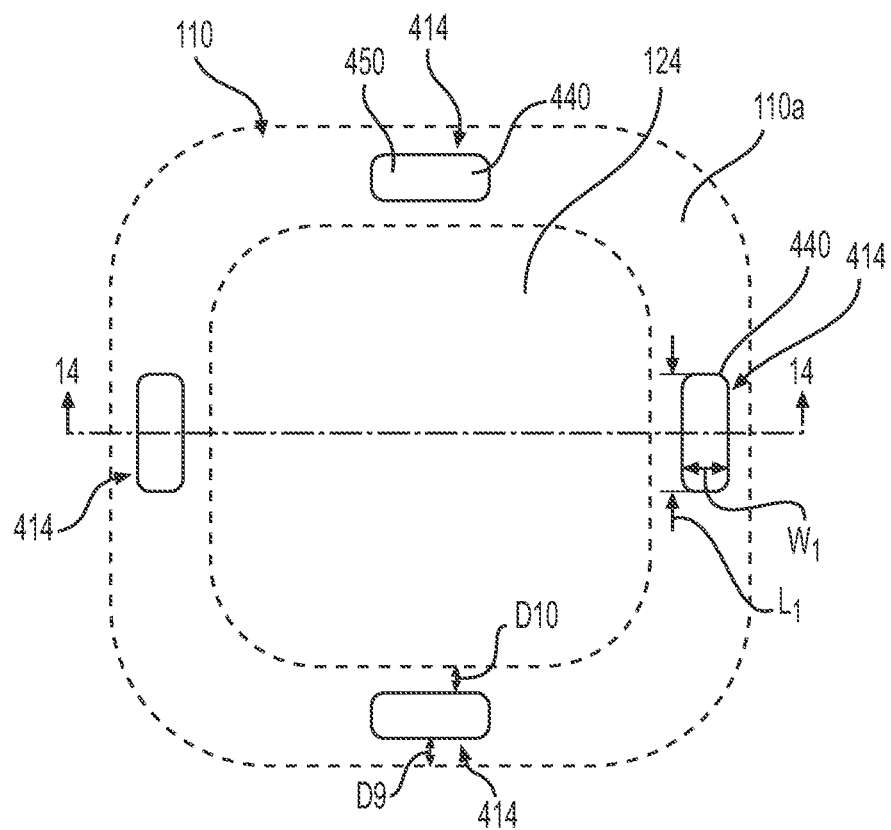
FIG. 13 is a top view of the physiological characteristic sensor assembly including the exemplary gravity resistance system of FIG. 12.

In one example, with reference to FIG. 13, the gravity resistance system 412 is shown in greater detail. FIG. 13 is a top view of the physiological characteristic sensor assembly 402, which illustrates the gravity resistance system 412 coupled to the adhesive patch 110. In this example, the gravity resistance system 412 includes a plurality of adhesive strips 414, which are spaced apart about a perimeter of the sensor base 124. The plurality of adhesive strips 414 is also spaced apart about a perimeter or circumference of the adhesive patch 110. In this example, the gravity resistance system 412 includes four adhesive strips 414, but it should be understood that the gravity resistance system 412 may include any number of adhesive strips 414.

Figure 14:
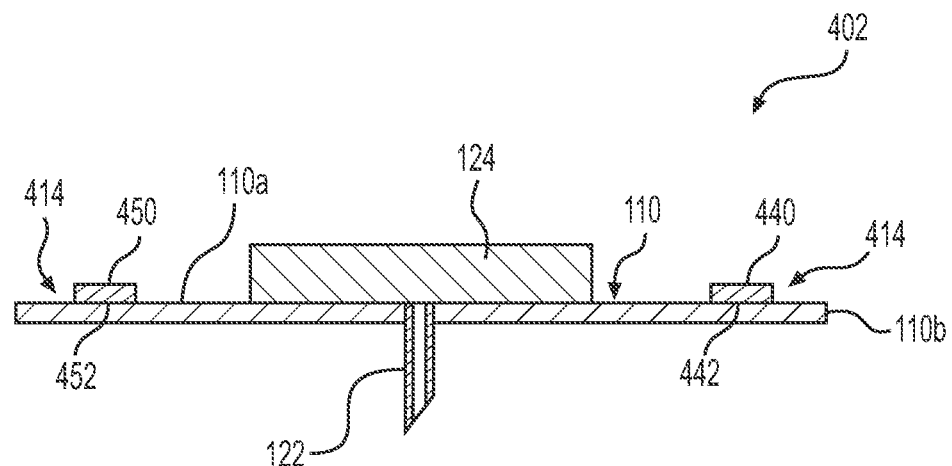
FIG. 14 is a cross-sectional view of the physiological characteristic sensor assembly including the exemplary gravity resistance system of FIG. 13, taken along line 14-14 of FIG. 13.

Each of the adhesive strips 414 includes a first, top surface 440 and a second, bottom surface 442 (FIG. 14). Each of the adhesive strips 414 is rectangular, with rounded edges. It should be noted, however, that the adhesive strips 414 may have any desired shape, and further, one or more of the adhesive strips 414 may have a different shape. In this example, each of the adhesive strips 414 has a length L1 and a width W1. The length L1 and width W1 are each predefined to ensure that the adhesive strips 414 provide rigidity to the adhesive patch 110, while also ensuring that the adhesive strips 414 do not interfere with the removal of the adhesive patch 110 from the sensor inserter 204, as will be discussed below. In one example, the length L1 is about 100 micrometers (μm) to about 1.0 millimeters (mm); and the width W1 is about 100 micrometers (μm) to about 5.0 millimeters (mm). Generally, the adhesive strips 414 are sized and located to interface with the monitor support 232. Each of the adhesive strips 414 is positioned a distance D9 from the perimeter 110b of the adhesive patch 110, and distance D10 from a perimeter of the sensor base 124. In one example, the distance D9 is about equal to or the same as the distance D10, and is about 0 millimeters (mm) to about 10 millimeters (mm).

In this example, each of the adhesive strips 414 comprises a differential double sided adhesive, which includes a high tack adhesive 450 on the top surface 440 and a low tack adhesive 452 on the bottom surface 442. The high tack adhesive 450 on the top surface 440 is coupled to the monitor support 232 (FIG. 12), and the low tack adhesive 452 on the bottom surface 442 is coupled to the adhesive patch 110. The top surface 440 of the gravity resistance system 412 is defined by the high tack adhesive 450 and the bottom surface 442 of the gravity resistance system 412 is defined by the low tack adhesive 452. In this example, high tack adhesive 450 and the low tack adhesive 452 are each coupled to or formed on opposed sides of a base layer. The base layer is composed of paper, poly-coated paper, polymers such as polyester film or HDPE film. In one example, the high tack adhesive 450 is composed of synthetic rubber adhesive, acrylic, etc. The high tack adhesive 450 may be cast, coated, painted or otherwise coupled to the base layer. The low tack adhesive 452 is coupled to or formed on a second, opposed side of the base layer. In one example, the low tack adhesive 452 is composed of silicone, acrylic, etc. The low tack adhesive 452 may be cast, coated, painted or otherwise coupled to the base layer. It should be noted that for ease of illustration, the base layer is not shown in the drawings as this paper or film layer has a predetermined nominal thickness.

In one example, with the physiological characteristic sensor 108 assembled and coupled to the adhesive patch 110 and the gravity resistance system 412 formed, with reference to FIG. 5, the adhesive strips 414 are coupled to the adhesive patch 110 (via the low tack adhesive 452 on the bottom surface 442) so as to be spaced apart about the perimeter 110b of the adhesive patch 110. With the physiological characteristic sensor assembly 402 assembled and the monitor support 232 coupled to the housing 230, the physiological characteristic sensor assembly 402 is coupled to the sensor inserter 204 such that the high tack adhesive 450 on the top surface 440 is coupled to the surface 232a of the monitor support 232. With the physiological characteristic sensor assembly 402 coupled to the monitor support 232, the cover 236 is coupled to the housing 230 to enclose the physiological characteristic sensor assembly 402. The sensor inserter 204, including the physiological characteristic sensor assembly 402, may be sterilized and shipped to an end user.

Once received, the user may remove the cover 236 to expose the physiological characteristic sensor assembly 402. The user may manipulate the sensor inserter 204 to deploy the physiological characteristic sensor assembly 402 onto the user. Once deployed, the high tack adhesive 450 on the top surface 440 retains the gravity resistance system 412 on the sensor inserter 204. Thus, the gravity resistance system 412 is removable from the adhesive patch 110 by the sensor inserter 204 upon deployment of the physiological characteristic sensor 108. The gravity resistance system 412 enables the sensor inserter 204 to be uncoupled from the physiological characteristic sensor 108 when the physiological characteristic sensor 108 is coupled to the user with the adhesive patch 110 without uncoupling the physiological characteristic sensor 108 and the adhesive patch 110 from the user.

By providing the adhesive strips 414 with the high tack adhesive layer 250 on the top surface 440 and the low tack adhesive 452 on the bottom surface 442, the gravity resistance system 412 is retained on the sensor inserter 204 and is removable from the physiological characteristic sensor 108 upon deployment without removing the adhesive patch 110 from the user. In addition, the gravity resistance system 412 allows for the use of larger adhesive patches 110, while inhibiting the drooping of the adhesive patch 110. In this regard, the gravity resistance system 412 adds structure and rigidity to the portion of the adhesive patch 110 that extends beyond the sensor base 124. Stated another way, the gravity resistance system 412 maintains the adhesive patch 110 substantially perpendicular to the longitudinal axis LA2 of the sensor inserter 204, which ensures the adhesive patch 110, when deployed, is properly coupled to the user.

Figure 15:
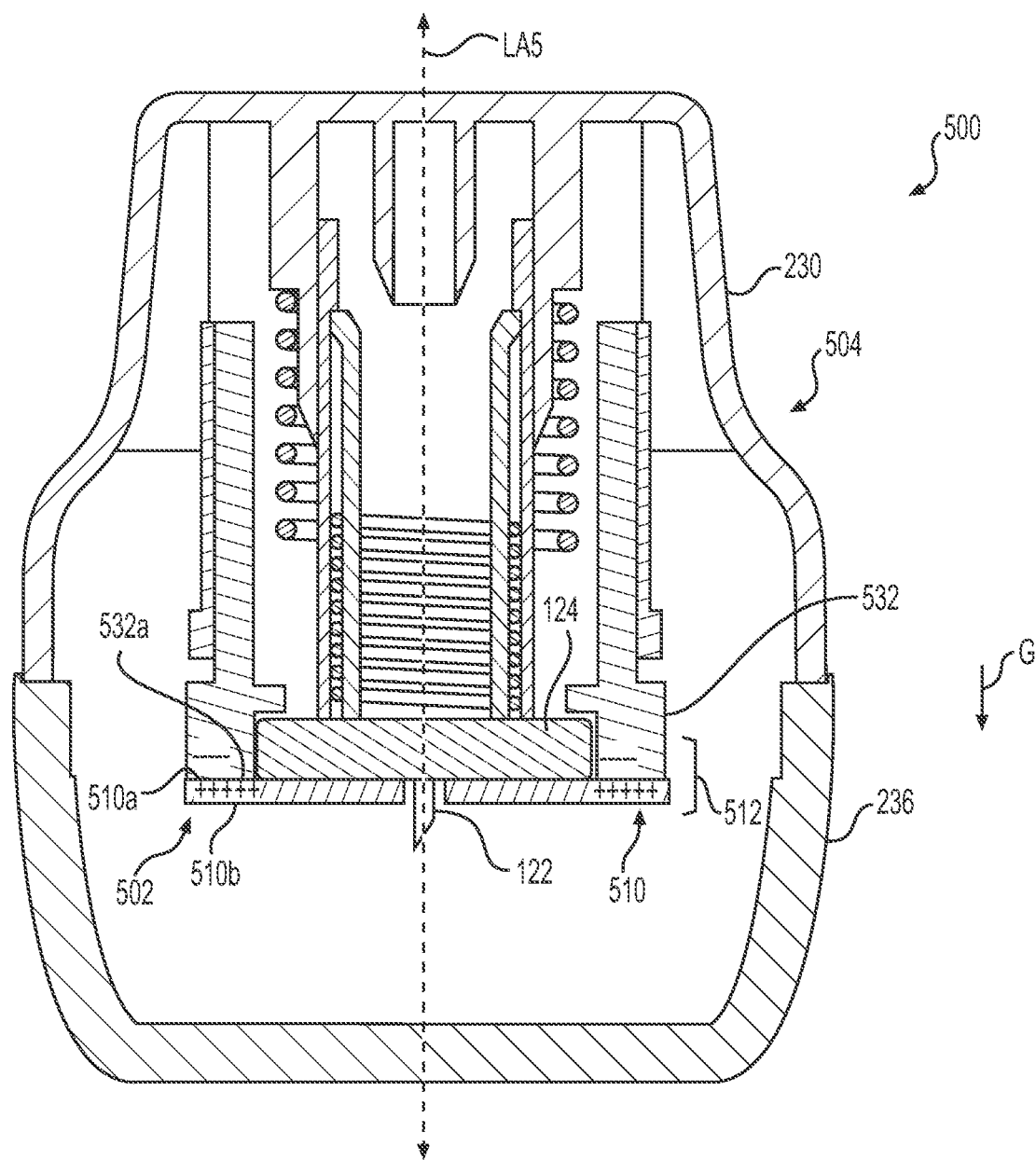
FIG. 15 is a cross-sectional view of another exemplary sensor introduction system that includes a sensor inserter and a physiological characteristic sensor assembly having an exemplary gravity resistance system according to various teachings of the present disclosure, taken from the perspective of line 2-2 of FIG. 1.

It should be noted that in other embodiments, the gravity resistance system 112 may be configured differently to inhibit or mitigate the effects of gravity on the adhesive patch 110. For example, with reference to FIG. 15, a sensor introduction assembly 500 is shown. As the sensor introduction assembly 500 includes the same or similar components as the sensor introduction assembly 100 discussed with regard to FIGS. 1-4 and the sensor introduction assembly 200 discussed with regard to FIGS. 5-8, the same reference numerals will be used to denote the same or similar components. FIG. 15 is a schematic cross-sectional view, taken from the perspective of line 2-2 of FIG. 1. In this example, the sensor introduction assembly 500 includes a physiological characteristic sensor assembly 502 and a sensor inserter 504. In this example, the physiological characteristic sensor assembly 502 includes the physiological characteristic sensor 108, an adhesive skin patch or adhesive patch 510 and a gravity resistance system 512. Generally, the components of the physiological characteristic sensor assembly 502 are coupled together as a single unit. The physiological characteristic sensor assembly 502 and the sensor inserter 504 may be packaged together for use by a consumer.

The physiological characteristic sensor 108 includes the glucose sensor 122 and the sensor base 124. Generally, the glucose sensor 122 is positionable in subcutaneous tissue of the user by an insertion needle of the sensor inserter 504 to measure the glucose oxidase enzyme. The sensor base 124 is coupled to the sensor inserter 504 and is coupled to the adhesive patch 110. The sensor base 124 is removably coupled to the sensor inserter 204.

The adhesive patch 510 is coupled to the sensor base 124 and affixes the sensor base 124, and thus, the glucose sensor 122, to the skin of the user. The adhesive patch 510 is contained within the sensor inserter 504 during packaging and shipping, and is exposed to the force of gravity G. The adhesive patch 510 may be composed of a flexible and breathable material with one or more adhesive layers, such as cloth, a bandage-like material, and the like. For example, suitable materials could include polyurethane, polyethylene, polyester, polypropylene, polytetrafluoroethylene (PTFE), or other polymers, to which one or more adhesive layers are applied. In this example, the adhesive patch 510 includes an electrically charged surface or first charged surface 510a. The first charged surface 510a is opposite the surface 510b, which is coupled to the user. In one example, the first charged surface 510a has a positive electric charge, which cooperates with a negatively charged surface of the sensor inserter 504, as will be discussed. In other examples, the first charged surface 510a may have a negatively charged surface, which cooperates with a corresponding positively charged surface of the sensor inserter 504. The first charged surface 510a may be charged using contact-induced charge separation, charge-induced charge separation, etc. For contact-induced charge separation, the amount of charge applied, and the polarity of the charge depends on the materials and surface roughness.

The sensor inserter 504 is coupled to the physiological characteristic sensor 108 and is manipulatable by a user to couple the glucose sensor 122 to the user. Briefly, the sensor inserter 504 includes the housing 230, a monitor support 532 and the lid or cover 236. In one example, the housing 230 surrounds the physiological characteristic sensor assembly 502 and encloses the physiological characteristic sensor assembly 502 to enable sterilization of the physiological characteristic sensor assembly 502, for example. The housing 230 may include one or more features that cooperate with the monitor support 532 to deploy the physiological characteristic sensor 108 into the anatomy. The monitor support 532 is coupled to the physiological characteristic sensor 108, and is manipulated by the user to deploy the physiological characteristic sensor 108 into the anatomy. In this example, the monitor support 532 includes an electrically charged surface or second charged surface 532a. The second charged surface 532a faces the adhesive patch 110. In one example, the second charged surface 532a has a negative electric charge, which cooperates with the first charged surface 510a of the adhesive patch 510. The second charged surface 532a may be charged using contact-induced charge separation, charge-induced charge separation, etc. For contact-induced charge separation, the amount of charge applied, and the polarity of the charge depends on the materials and surface roughness.

In the example of contact-induced charge separation, the first charged surface 510a of the adhesive patch 510 is composed of a material that is more negatively charged in the triboelectric series, such as a polyurethane film. The second charged surface 532a of the monitor support 532 is composed of a material that is more positively charged in the triboelectric series than the material of the first charged surface 510a of the adhesive patch 510, such as a nylon. The contact between the first charged surface 510a and the second charged surface 532a results in adhesion between the two surfaces 510a, 532a as the electrons are exchanged and are attracted to one another by opposite charge build up on each surface, which inhibits the drooping of the adhesive patch 510. It should be noted that the materials selected herein are merely examples, as any materials that are separated along the triboelectric series relative to one another may be used for the adhesive patch 510 and the monitor support 532 so long as the contact between the first charged surface 510a and the second charged surface 532a results in adhesion between the two surfaces 510a, 532a due to electron exchange and attraction due to opposite charge build up on the respective surfaces 510a, 532a. It should be noted that an entirety of the monitor support 532 may be composed of the predetermined material, or merely a surface of the monitor support 532, such as the second charged surface 532a, may be formed of the predetermined material.

In the example of charge-induced charge separation, the first charged surface 510a may be initially composed of an electrically neutral material such as polyester that has been electrically grounded to have a net neutral charge. A negatively charged object may be brought near the first charged surface 510a, to induce a positive charge on the first charged surface 510a as the positive electrons associated with the first charged surface 510a move toward the negatively charged object. Similarly, the second charged surface 532a may be composed of an electrically neutral material such as polycarbonate that has been electrically grounded to have a net neutral charge. A positively charged object may be brought near the second charged surface 532a, to induce a negative charge on the second charged surface 532a as the negative electrons associated with the first charged surface 510a move toward the positively charged object. When the physiological characteristic sensor 108 is coupled to the sensor inserter 504, the negatively-charged second charged surface 532a attracts the positively-charged first charged surface 510a, which inhibits the drooping of the adhesive patch 510.

The cover 236 surrounds the circumferentially open end of the housing 230, and encloses the housing 230. Generally, the cover 236 is coupled to the housing 230 such that the adhesive patch 510 is unsupported by the cover 236. As discussed, the gravity resistance system 512 inhibits or mitigates the force of gravity G from pulling down on the unsupported adhesive patch 510, which in turn, inhibits or mitigates the drooping or sagging of the adhesive patch 510 within the sensor inserter 204 ensuring full contact is made between an entirety of the adhesive patch 510 and the anatomy of the user.

In one example, with the physiological characteristic sensor 108 assembled and coupled to the adhesive patch 510 and the gravity resistance system 512 formed, the first charged surface 510a is charged to have the respective electric charge, in this example, a positive electric charge. The second charged surface 532a of the monitor support 532 is charged to have the respective electric charge, in this example, a negative electric charge. With the physiological characteristic sensor assembly 502 assembled and the monitor support 532 coupled to the housing 230, the physiological characteristic sensor assembly 502 is coupled to the sensor inserter 504 such that the first charged surface 510a of the adhesive patch 510 is electrically attracted to the second charged surface 532a of the monitor support 532. With the physiological characteristic sensor assembly 502 coupled to the monitor support 532, the cover 236 is coupled to the housing 230 to enclose the physiological characteristic sensor assembly 502. The sensor inserter 504, including the physiological characteristic sensor assembly 502, may be sterilized and shipped to an end user.

Once received, the user may remove the cover 236 to expose the physiological characteristic sensor assembly 502. The user may manipulate the sensor inserter 504 to deploy the physiological characteristic sensor assembly 502 onto the user. The weak attractive force between the first charged surface 510a and the second charged surface 532a enables the sensor inserter 504 to be removed from the physiological characteristic sensor assembly 502. Thus, the gravity resistance system 512 enables the sensor inserter 504 to be uncoupled from the physiological characteristic sensor 108 when the physiological characteristic sensor 108 is coupled to the user with the adhesive patch 510 without uncoupling the physiological characteristic sensor 108 and the adhesive patch 510 from the user. Further, by providing the attractive force between the first charged surface 510a and the second charged surface 532a, the gravity resistance system 512 allows for the use of larger adhesive patches 110, while inhibiting the drooping of the adhesive patch 510. In this regard, the attractive force between the first charged surface 510a and the second charged surface 532a maintains the adhesive patch 510 substantially perpendicular to a longitudinal axis LA5 of the sensor inserter 504, which ensures the adhesive patch 510, when deployed, is properly coupled to the user. Stated another way, the adhesive patch 510 includes a first electrically charged surface or the first charged surface 510a having a first electric charge, which in this example is a positive electric charge, the sensor inserter 504 includes a second electrically charged surface or the second charged surface 532a having a second electric charge, which in this example is a negative electric charge, and the first electric charge is different than the second electric charge to maintain the adhesive patch 510 substantially perpendicular to the longitudinal axis LA5 of the sensor inserter 504.

It should be noted that the sensor inserter 104, 204, 504 described and illustrated herein is merely exemplary, as any device may be employed with the gravity resistance system 112, 212, 312, 412, 512 to deploy the physiological characteristic sensor 108 into the anatomy. For example, an exemplary sensor inserter may include merely a monitor support, such as the monitor support 232, 532, which is manually manipulated by a user to deploy the physiological characteristic sensor 108 into the anatomy. Moreover, it should be noted that the sensor inserter 204, 504 may comprise the sensor inserter 104 discussed with regard to FIGS. 1-4 or the insertion device described in commonly assigned U.S. Patent Publication No. 2017/0290533 to Antonio, et al., the relevant portion of which was previously incorporated herein by reference.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A system comprising:
a physiological characteristic sensor having a sensor base;
a sensor inserter including a support coupled to the physiological characteristic sensor and the support is movable to deploy the physiological characteristic sensor;
an adhesive patch coupled to the sensor base of the physiological characteristic sensor, the adhesive patch having a first surface and a second surface opposite the first surface, the second surface configured to couple the physiological characteristic sensor to an anatomy upon deployment; and
a gravity resistance system including a first tack adhesive coupled to the support of the sensor inserter and a second tack adhesive coupled to the first surface of the adhesive patch so as to be spaced apart from the sensor base, the second tack adhesive less tacky than the first tack adhesive, the gravity resistance system maintains the adhesive patch substantially perpendicular to a longitudinal axis of the sensor inserter prior to deployment of the physiological characteristic sensor and is removable from the adhesive patch by the sensor inserter upon deployment of the physiological characteristic sensor.

2. The system of claim 1, wherein the gravity resistance system is a double sided adhesive such that the first tack adhesive is opposite the second tack adhesive.

3. The system of claim 2, wherein the gravity resistance system comprises a plurality of adhesive strips, each adhesive strip of the plurality of adhesive strips including the first tack adhesive opposite the second tack adhesive, which are spaced apart about a perimeter of the adhesive patch and the sensor base is coupled to the first surface of the adhesive patch.

4. The system of claim 1, wherein the gravity resistance system comprises a first adhesive layer with the first tack adhesive on opposed sides, and a second adhesive layer with the second tack adhesive on opposed sides.

5. A system comprising:
a physiological characteristic sensor having a sensor base and a sensor that extends from the sensor base;
a sensor inserter including a support coupled to the physiological characteristic sensor and the support is movable to deploy the physiological characteristic sensor;
an adhesive patch coupled to the sensor base of the physiological characteristic sensor, the adhesive patch having a first surface and a second surface opposite the first surface, the second surface configured to couple the physiological characteristic sensor to the anatomy upon deployment; and a gravity resistance system coupled to the first surface of the adhesive patch and to the support of the sensor inserter, the gravity resistance system including at least one adhesive layer, the at least one adhesive layer including a first tack adhesive coupled to the support of the sensor inserter and a second tack adhesive coupled to the first surface of the adhesive patch so as to be positioned about at least a portion of a perimeter of the adhesive patch and spaced apart from the sensor base, the second tack adhesive less tacky than the first tack adhesive, and the gravity resistance system maintains the adhesive patch substantially perpendicular to a longitudinal axis of the sensor inserter prior to deployment of the physiological characteristic sensor and is removable from the adhesive patch by the sensor inserter upon deployment of the physiological characteristic sensor.

6. The system of claim 5, wherein the at least one adhesive layer is a double sided adhesive and comprises a plurality of adhesive strips, which are spaced apart about the perimeter of the adhesive patch and the sensor base is coupled to the first surface of the adhesive patch.

7. The system of claim 5, wherein the at least one adhesive layer is a double sided adhesive layer.

8. The system of claim 5, wherein the at least one adhesive layer of the gravity resistance system comprises a plurality of adhesive layers with a first one of the plurality of adhesive layers comprising the first tack adhesive on opposed sides, and a second one of the plurality of adhesive layers comprising the second tack adhesive on opposed sides.

9. A system comprising:
a physiological characteristic sensor having a sensor base including a sensor, the sensor extends from the sensor base and is configured to be inserted within an anatomy;
a sensor inserter including a support coupled to the physiological characteristic sensor and the support is movable to deploy the physiological characteristic sensor;
an adhesive patch coupled to the sensor base of the physiological characteristic sensor, the adhesive patch having a first surface and a second surface opposite the first surface, the sensor base coupled to the first surface, and the second surface is configured to couple the physiological characteristic sensor to an anatomy upon deployment; and
a gravity resistance system coupled to the first surface of the adhesive patch and to the support of the sensor inserter, the gravity resistance system including at least one adhesive layer, the at least one adhesive layer coupled to the first surface of the adhesive patch so as to be positioned about a perimeter of the adhesive patch and spaced apart from the sensor base by a distance, the at least one adhesive layer comprises a first tack adhesive on a first side and a second tack adhesive on a second side, the second side opposite the first side, the second tack adhesive less tacky than the first tack adhesive, the first tack adhesive coupled to the support and the second tack adhesive coupled to the first surface of the adhesive patch, and the gravity resistance system maintains the adhesive patch substantially perpendicular to a longitudinal axis of the sensor inserter prior to deployment of the physiological characteristic sensor and is removable from the adhesive patch by the sensor inserter upon deployment of the physiological characteristic sensor.

10. The system of claim 9, wherein the at least one adhesive layer of the gravity resistance system comprises a plurality of adhesive layers coupled between a surface of the adhesive patch and a surface of the sensor inserter with a first one of the plurality of adhesive layers comprising the first tack adhesive that defines the first side, and a second one of the plurality of adhesive layers comprising the second tack adhesive that defines the second side.

* * * * *